United States Patent
Sakashita

(10) Patent No.: US 9,844,316 B2
(45) Date of Patent: Dec. 19, 2017

(54) CORNEAL ENDOTHELIAL CELL ANALYSIS METHOD AND CORNEAL ENDOTHELIAL CELL ANALYSIS APPARATUS

(71) Applicant: NIDEK CO., LTD., Gamagori-shi, Aichi (JP)

(72) Inventor: Yusuke Sakashita, Okazaki (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 14/715,215

(22) Filed: May 18, 2015

(65) Prior Publication Data

US 2015/0327758 A1 Nov. 19, 2015

(30) Foreign Application Priority Data

May 19, 2014 (JP) ................. 2014-102955

(51) Int. Cl.
*A61B 3/14* (2006.01)
*A61B 3/10* (2006.01)
*A61B 3/00* (2006.01)

(52) U.S. Cl.
CPC .......... *A61B 3/0033* (2013.01); *A61B 3/0025* (2013.01); *A61B 3/0058* (2013.01)

(58) Field of Classification Search
CPC ........... A61B 3/14; A61B 3/103; A61B 3/113; A61B 3/1208; A61B 3/1225; A61B 3/024; A61B 3/032; A61B 3/1015
USPC ................ 351/206, 200, 205, 209–211, 218, 351/221–223, 246
See application file for complete search history.

(56) References Cited

U.S. PATENT DOCUMENTS

| 6,164,778 A | 12/2000 | Takagi et al. |
| 6,234,630 B1 | 5/2001 | Nishio |
| 2013/0286350 A1 | 10/2013 | Sakashita et al. |
| 2014/0016094 A1* | 1/2014 | Sakashita ................. A61B 3/14 351/206 |
| 2016/0128564 A1* | 5/2016 | Oe ....................... A61B 3/1005 351/208 |

FOREIGN PATENT DOCUMENTS

JP 2014-018226 A 2/2014

* cited by examiner

*Primary Examiner* — Dawayne A Pinkney
(74) *Attorney, Agent, or Firm* — Oliff PLC

(57) ABSTRACT

A corneal endothelial cell analysis method includes: a step of displaying a photographed image including endothelial cells of a cornea of an examinee's eye on a monitor; a step of setting, based on an operation signal from a user interface, regions of the endothelial cells for each or more than one of the cells with respect to the photographed image displayed on the monitor, the setting step including setting the endothelial cell regions on the one photographed image by use of setting modes including at least a first setting mode of setting the endothelial cell regions and a second setting mode different from the first setting mode; and a step of obtaining an analysis result on the endothelial cells of the examinee's eye based on the endothelial cell regions set by the first setting mode and the endothelial cell regions set by the second setting mode.

11 Claims, 6 Drawing Sheets

CORNEAL ENDOTHELIAL CELL ANALYSIS METHOD AND CORNEAL ENDOTHELIAL CELL ANALYSIS APPARATUS

CROSS-REFERENCE TO RELATED APPLICATIONS

This application is based upon and claims the benefit of priority from the prior Japanese Patent Applications No. 2014-102955 filed on May 19, 2014, the entire contents of which are incorporated herein by reference.

BACKGROUND

This disclosure relates to a corneal endothelial cell analysis method and a corneal endothelial cell analysis apparatus for analyzing corneal endothelial cells of an examinee's eye.

There is conventionally known an apparatus for analyzing an endothelial cell image photographed by use of reflection light from endothelial cells of a cornea (see Patent Document 1). The apparatus of this type is operated for manual analysis in some cases. In the manual analysis, an examiner inputs a position at which endothelial cells are identified in an endothelial cell image displayed on a monitor, and the analysis is performed on the assumption that the cells are present in that input position. As the manual analysis method, for example, there are known various analysis methods such as a center method, an apex input method, a grid method, and a trace method.

RELATED ART DOCUMENTS

Patent Documents

Patent Document 1: JP-A-2014-018226

SUMMARY

However, the manual analysis differs in analysis workability, correctness of analysis results, and others according to the analysis methods. In some analysis methods, it may be difficult to analyze an eye having abnormal endothelium (e.g., a diseased eye). It would be difficult for one type of manual analysis to analyze different endothelial cell images well according to a diseased eye of an examinee's eye.

This disclosure has been made in view of the conventional problems and has a purpose to provide a corneal endothelial cell analysis method and apparatus capable of analyzing endothelial cells of an examinee's eye well.

A first aspect of the present disclosure provides a corneal endothelial cell analysis method comprising: a displaying step of displaying a photographed image including endothelial cells of a cornea of an examinee's eye on a monitor; a setting step of setting, based on an operation signal from a user interface, regions of the endothelial cells for each or more than one of the cells with respect to the photographed image displayed on the monitor, the setting step including setting the regions of the endothelial cells on the one photographed image by use of a plurality of setting modes including at least a first setting mode of setting the regions of the endothelial cells and a second setting mode different from the first setting mode; and an analysis result obtaining step of obtaining an analysis result on the endothelial cells of the examinee's eye based on the regions of the endothelial cells set by the first setting mode in the setting step and the regions of the endothelial cells set by the second setting mode in the setting step.

A second aspect of the present disclosure provides a corneal endothelial cell analysis method comprising: a displaying step of displaying a photographed image including endothelial cells of a cornea of an examinee's eye on a monitor; a detection range setting step of setting a detection range in which the region of each of the endothelial cells in the photographed image is to be detected, based on a first operation signal from the user interface; a detection-processing step of processing the photographed image to detect the region of each of the endothelial cells included in the detection range from the detection range set in the detection range setting step; a setting step of setting the regions of the endothelial cells for each or more than one of the cells with respect to the photographed image displayed on the monitor, based on a second operation signal from the user interface; and an analysis result obtaining step of obtaining an analysis result on the endothelial cells of the examinee's eye based on the regions of the endothelial cells detected in the detection-processing step and the regions of the endothelial cells set in the setting step with respect to the one photographed image.

DETAILED DESCRIPTION OF THE EXEMPLARY EMBODIMENTS

Figure 1:
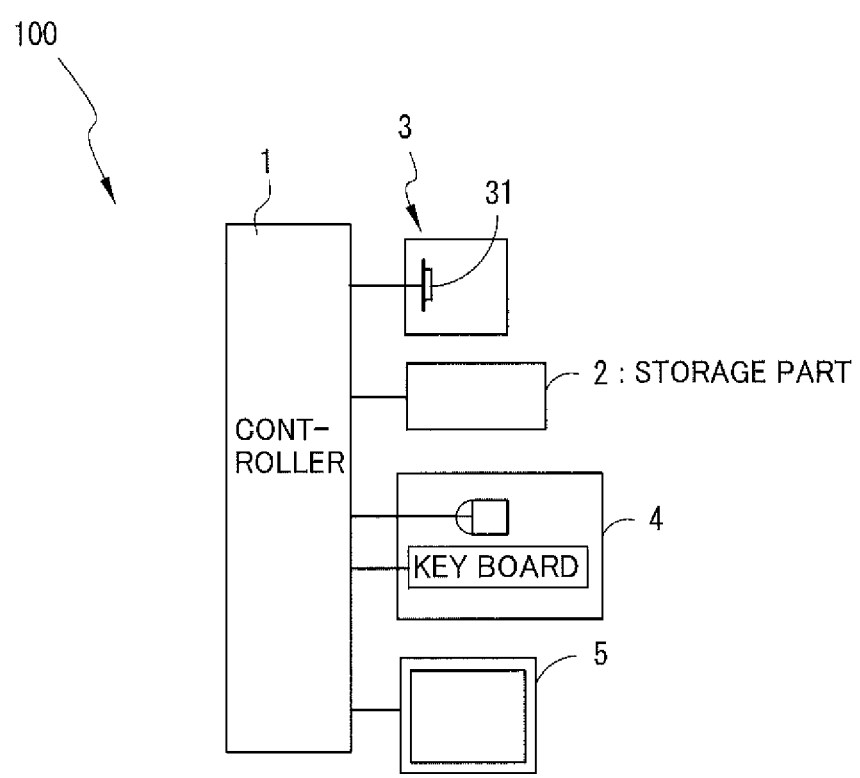
FIG. 1 is a diagram showing a schematic structure of a cornea endothelial cell analysis apparatus in an embodiment.

A typical embodiment of the present disclosure will be described below referring to accompanying drawings. A first embodiment of the present disclosure will be explained first referring to FIGS. 1 to 7. FIG. 1 is a schematic configuration view of a cornea endothelial cell analysis apparatus 100 (hereinafter, simply referred to as an "analysis apparatus 100"). This analysis apparatus 100 includes a control part (a processor, a controller) 1, a storage part (a memory) 2, a photographing part 3, an operation input part (hereinafter, simply referred to as an input part) 4, a monitor 5, and others. Each of these components is connected to the analysis apparatus 100 via bus or the like.

Each part of the analysis apparatus 100 is controlled by the control part 1. The control part 1, which will be described in detail later, executes an endothelial image analysis program to analyze a photographed image 201 including endothelial cells (see FIG. 2). Accordingly, the control part 1 outputs an analysis result related to for example at least one of the number of endothelial cells included in the photographed endothelial cell image, cell density, cell area, hexagonal cell appearance rate, and others. The endothelial cell image analysis program is stored in the storage part (memory) 2. This storage part 2 may include for example a semiconductor memory, a magnetic storage device, an optical storage device, and others.

The photographing part 3 is configured to photograph a cornea portion of an eye in a non-contact manner. This photographing part 3 is provided with a photographing optical system for capturing an endothelial cell image of an examinee's eye by receiving reflection light from a cornea. The photographing optical system is provided with at least a two-dimensional imaging element 31 (hereinafter, simply referred to as an "imaging element 31"). In the present embodiment, the control part 1 obtains an endothelial cell image based on a signal (image data) output from the imaging element 31. The control part 1 stores the obtained endothelial cell image in the storage part 2. The control part 1 also reads out an endothelial cell image (a static image) from the storage part 2 and displays it on a monitor 5.

This apparatus 100 also may further include an alignment detection optical system for detecting an alignment state with respect to corneal endothelium, an anterior segment observation optical system for allowing observation of an anterior segment of the examinee's eye, and others. For the detailed structure of optical systems which can be included in the photographing part 3, refer to Patent Document 1 and others.

The input part 4 is an input device (a user interface) to be operated by an examiner. The input part 4 may include a switch, a keyboard, a pointing device (e.g., a mouse and a touch panel/screen), and others. The control part 1 receives a command from the examiner by receiving a signal output from the input part 4 in response to the operation of an examiner.

The monitor 5 is used as an information output device and is controlled by the control part 1. The monitor 5 in the present embodiment is a touch panel allowing an examiner to perform input operation and functions as the input part 4.

<Basic Screen for Analysis>

An operation of analyzing an endothelial cell image by the analysis apparatus 100 will be explained below, referring to FIGS. 2 to 7.

Figure 2:
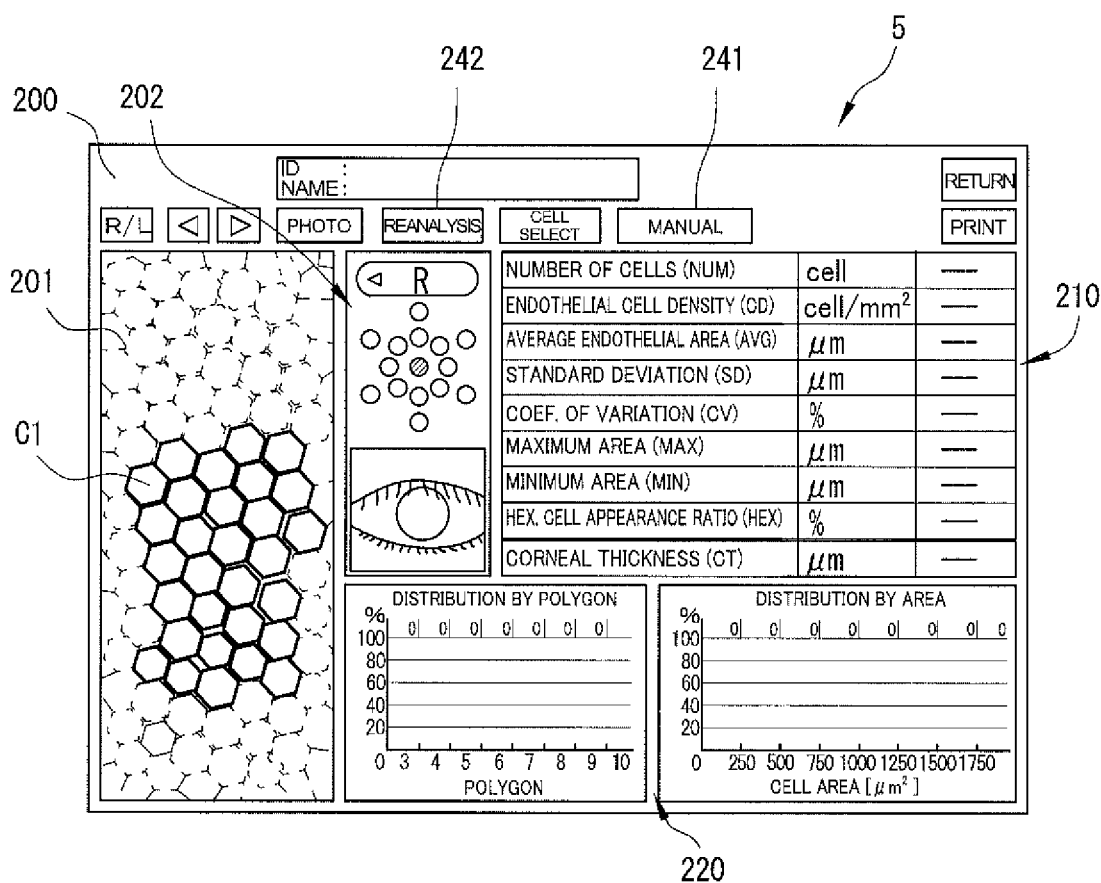
FIG. 2 is a schematic diagram showing a basic screen configuration for analysis.

FIG. 2 is a schematic diagram showing a basic screen configuration for analysis. On a basic screen 200 of the monitor 5, there are displayed a cornea endothelial cell image 201 of an examinee's eye and a photographed eye information display section 202, an analysis result display section 210, a distribution graph display section 220, various types of operation buttons, and others. A display layout is not limited to the arrangement shown in FIG. 2.

The endothelial cell image 201 is an endothelial cell image of an examinee's eye photographed by a cornea endothelial cell photographing apparatus and normally contains a plurality of endothelial cells distributed two-dimensionally. The photographed eye information display section 202 displays photographed eye information (e.g., right and left eyes, fixation lamp lighting positions, anterior segment image, etc.) of the endothelial cell image 201. The analysis result display section 210 displays an analysis result on the endothelial cell image 201. As the analysis result, for example, there is displayed at least one of endothelial cell density, average endothelial cell area, standard deviation of endothelial area, coefficient of variation of endothelial area, maximum area, minimum area, appearance ratio of hexagonal cells, and others. The distribution graph display section 220 displays a histogram showing the distribution of variations in rectangular shape, variations in cell area, and others.

In the present embodiment, in the initial state of the basic screen 200, results of automatic analysis performed by the control part 1 with respect to the whole range of the displayed endothelial cell image 201 are displayed on the analysis result display section 210 and the distribution graph display section 220. In the automatic analysis, the endothelial cell image 201 displayed on the monitor 5 is processed by the control part 1, so that a region of each endothelial cell included in the whole range of the photographed image 201. In the present embodiment, the control part 1 displays by superimposing a cell image C1 indicating the region of an endothelial cell on a detection position of each endothelial cell in the endothelial cell image 201. The analysis result display section 210 in the initial state also displays an analysis result based on the detected regions of endothelial cells. However, detection and analysis of the endothelial cells in the photography image 201 may not be performed in advance in the initial state. For instance, the automatic analysis of endothelial cells may be executed at a timing when a command for executing automatic analysis is input by an examiner to the control part 1 via the input part 4.

Meanwhile, in the case of measuring an eye whose corneal endothelium is difficult to photograph (e.g., a diseased eye), the number of cells in one image may be very small. For instance, in some conceivable cases, the number of endothelial cells is actually small, and the recognizable range of endothelial cells is limited. For the automatic analysis, the number of cells of corneal endothelium is preferably not less than 100 at the minimum. However, in the case of a diseased eye, it is not uncommon found that the number of detected cells is 50 or less. In the above conventional case, the automatic analysis is unlikely to detect the cells and thus the manual analysis needs be performed.

An examiner judges the necessity of manual analysis from the endothelial image 201, the cell image C1 superimposed on the endothelial image 201, the automatic analysis results and others displayed in the analysis result display section 210.

On the basic screen 200, various operation buttons are displayed. One of the buttons is a manual analysis button 241. At the touch of this manual analysis button 241, a manual analysis screen 260 (see FIGS. 3 and 6) appears. The displayed analysis results are not limited to those in the present embodiment.

<Manual Analysis>

Figure 3:
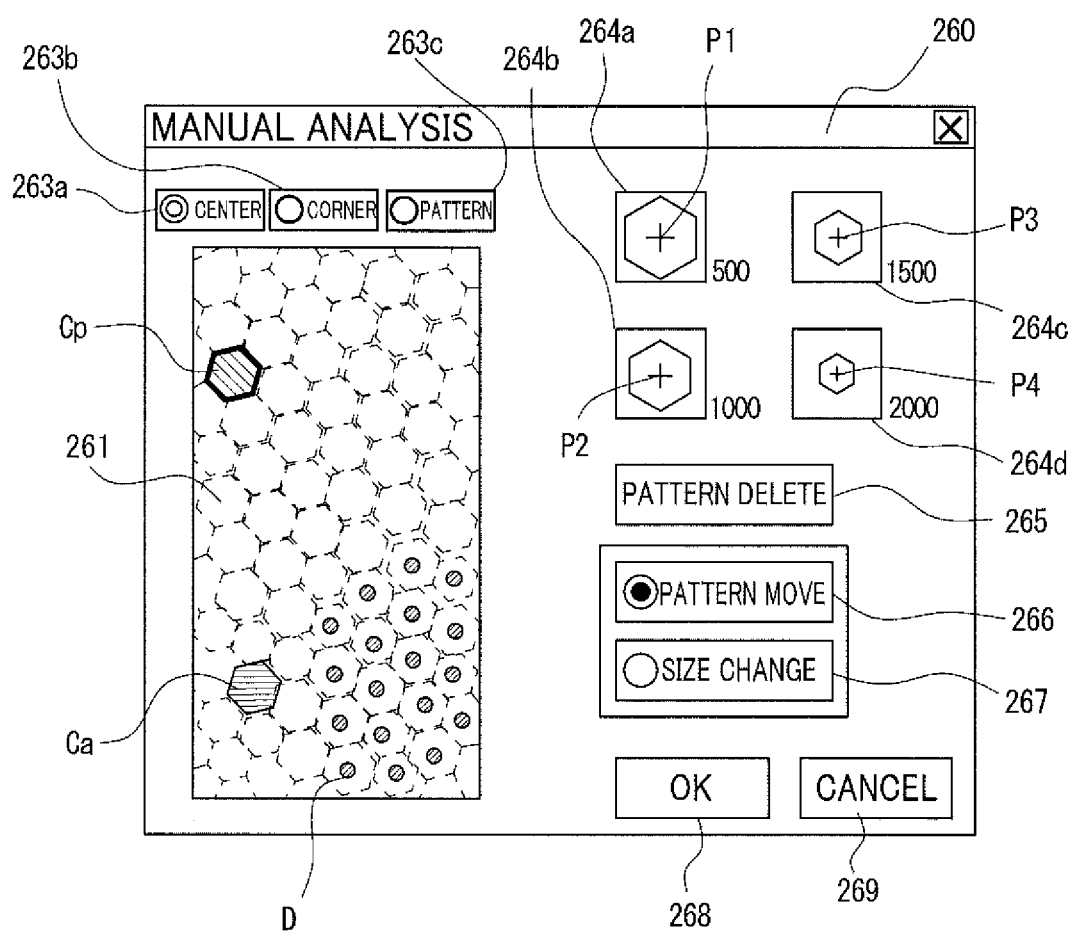
FIG. 3 is a schematic diagram showing a manual analysis screen.

Herein, referring to FIG. 3, the manual analysis operation of endothelial cells to be executed in the analysis apparatus 100 in the first embodiment will be described. In FIG. 3, explanation is made on the case where automatic analysis results are not taken account (in the present embodiment, for instance, the case where any endothelial cells are not detected at all by automatic analysis, the case where detection results of endothelial cells by automatic analysis have been cleared, and other cases). The case of integrating the automatic analysis results and the manual analysis results will be described later with reference to FIG. 6.

In a manual analysis screen 260 in FIG. 3, an endothelial cell image 261 is displayed on a left side. This endothelial cell image 261 is the same photographed image as the endothelial cell image 201 in FIG. 2 and represents the same range in the present embodiment. Above the endothelial cell image 261, there are displayed setting mode select buttons 263a, 263b, and 263c, that is, a center method select button 263a, an apex input method (a corner point method) select button 263b, and a pattern selecting method select button 263c. In the present embodiment, these three buttons 263a, 263b, and 263c correspond to three different types of manual analysis in the present embodiment. The three types of manual analysis are different from each other in setting mode (estimating mode) for setting (or estimating) a region of endothelial cells targeted for analysis by manual operation. It is to be noted that the setting mode(s) of cell regions usable in the analysis apparatus 100 may be two kinds of modes or four or more kinds of modes.

As the setting mode of cell regions, for example, a profile (boundary) of each cell is set. To be concrete, the different setting modes are different in setting target defined based on commands input by an examiner, for example. The setting targets can be set in units of cell and will be defined according to input command. As the setting target, for example, at least one of the center of each cell, the apex of each cell, one side of a cell, the whole area of each cell is defined according to the input command. The defined setting target is used as a base in setting a region of each endothelial cell. Thus, an examiner can set a region of each cell according to workability and a disease type of an examinee's eye. When the setting targets are different, different arithmetic processing is made to set the profile (boundary) of the endothelial cells. Accordingly, respective arithmetic modes may be prepared.

In the present embodiment, when any one of the buttons 263a, 263b, and 263c is decided or changed (for example, by touching), the setting mode in the manual analysis (that is, the setting method of the region of endothelial cell) is selected or changed. In the present embodiment, the setting mode is chosen from among the center method, the apex input method (the corner point method), and the pattern selecting method. However, the setting method is not limited to the above-described examples and may be chosen for example from other methods such as a grid method and a trace method. In this case, in terms of the reliability of analysis results and the efficiency of input operation, various types of setting modes are prepared in consideration of the property of each setting mode.

The control part 1 in the present embodiment is configured to set a region of an endothelial cell by any one of the plurality of setting modes mentioned above. Further, this setting of the endothelial cell region is performed for at least each one of the endothelial cells based on a command (i.e., an operation signal from the input part 4) input to the control part 1 by an examiner. The command may be for example a command to set an endothelial cell region (e.g., designating the center point of a cell, the profile or apex of a cell, designating a reference position at which a reference pattern is placed, and others).

When the center method select button 263a is touched, the center method is selected as the cell-region setting mode. The center method is a method in which when the positions (or the coordinates) of center points of a plurality of two-dimensionally contiguous endothelial cells are input, the profile (boundary) of a region of an endothelial cell having a first center point is estimated based on a positional relationship between the first center point and second center points present around the first center point (referred to as peripheral points). In the present embodiment, the region surrounded by the estimated profile is explained as the endothelial cell region to be set by the center method. In the present embodiment, while the center method is being selected, when the center points of endothelial cells in the endothelial cell image 261 on the monitor 5 are touched, the positions of the center points are indicated to the control part 1. In the present embodiment, the control part 1 displays a mark D such as a dot by superimposing at the position of each center point indicated in the endothelial cell image 261 (see FIG. 3). After the marks D are set with respect to the plurality of endothelial cells two-dimensionally contiguous in the endothelial cell image 261, when an OK button 268 is touched, the control part 1 sets the profile of each endothelial cell region based on the positional relationship of their center points and analyzes the endothelial cells. In the present embodiment, after analysis, the control part 1 displays by superimposing a cell image C (a cell image Cc) representing an endothelial cell on the region of the endothelial cell whose profile has been set in the endothelial cell image 261 (see FIG. 4).

In the center method, accordingly, as long as the positions of the center points of endothelial cells are indicated by an examiner, the region of each endothelial cell is set. Accordingly, the center method provides advantages in less burden of input operation on an examiner as compared with other setting modes which will be described later. On the other hand, it is impossible to estimate the profile for the first center point around which sufficient peripheral points are not present. Therefore, a good analysis result cannot be obtained unless a range includes a relatively large number of cells closely packed. Depending on a disease type of an examinee's eye, the cells may be not tightly packed in a range allowing execution of the center method and may be formed apart from each other. In this case, it is difficult to obtain a highly reliable result by the center method. For the details of the center method, refer to Japanese patent No. 3265044 and others, for example.

When the apex input method select button 263b is touched, the apex input method is set as the cell-region setting mode. In the apex input method, the control part 1 receives the input by an examiner on the apex position of each endothelial cell (concretely, the coordinate of each apex of the cell profile). In the present embodiment, when an examiner touches the apexes (corners) of one endothelial cell included in the endothelial cell image 261 in order clockwise (or counterclockwise) on the monitor 5 and then touches the first input apex again, the control part 1 specifies (sets) the profile of the region of one endothelial cell surrounded by a series of the apexes. Further, the control part 1 displays by superimposing the cell image C (a cell image Ca) representing the endothelial cell whose region has been set by the apex input method on the endothelial cell each apex of which has been input in the endothelial cell image 261 (see FIG. 3). When the OK button 268 is touched on the monitor 5 after at least one cell image Ca is displayed by superimposing, the control part 1 analyzes the endothelial cell whose apexes have been input. According to the apex input method, as above, the positions of a plurality of points (i.e., each apex of the profile of an endothelial cell) are requested to specify one endothelial cell. This causes a larger burden of the input operation on the examiner than in the center method. However, according to the apex input method, for even a cell image of the cells that are not tightly packed but are formed apart from each other (that is, an image difficult to analyze by the center method only), a region of an endothelial cell can be appropriately set. Further, this method is advantageous in a case where a cell shape is so special as to make difficult to define the boundary of the cell by a simple pattern.

When the pattern selecting method select button 263c is touched, the pattern selecting method is chosen as the setting mode of manual analysis. In the pattern selecting method, a cell image Cp based on a reference pattern P (P1-P4) is displayed by superimposing on the endothelial cell included in the endothelial cell image 261 by utilizing patterns of endothelial cell regions prepared in advance (hereinafter, referred to as "reference pattern P"). In the pattern selecting method, the endothelial cell region is set on a region superimposed by the cell image Cp.

In an example of FIG. 3, on the right side of the endothelial cell image 261, pattern select buttons 264a to 264d are provided to select the reference pattern P having a size corresponding to the endothelial cell from among the reference patterns P1 to P4 different in size. After any one of the reference patterns P1 to P4 is selected by touch operation on one of the pattern select buttons 264a to 264d, the examiner inputs a command representing the position at which the cell image Cp is to be set in the endothelial cell image 261 to the control part 1 via the input part 4. The control part 1 displays by superimposing the cell image Cp having the same size as the reference pattern image at the designated position on the endothelial cell image 261. In the example of FIG. 3, even though the detailed explanation is omitted, a pattern delete button 265, a pattern move button 266, and a size change button 267 are arranged below the pattern select buttons 264a to 264d. By appropriate operation of these buttons 265 to 267, the cell image Cp displayed once by superimposing on the endothelial cell image 261 will be deleted, moved, or changed in size. When at least one cell image Cp is set in the endothelial cell image 261 and then the OK button 268 is touched, the control part 1 specifies (sets) the profile of the endothelial cell based on the boundary position of the cell image Cp. The control part 1 executes the analysis of endothelial cell based on the specified profile information.

According to the pattern selecting method, for even the cell image of the cells not closely packed, but formed apart from each other (that is, the image difficult to analyze by the center method only), the endothelial cell region can be appropriately set.

According to the pattern selecting method, when many of the cells have general shapes and coincide with a predetermined pattern, the input operation can be simplified. Specifically, the pattern selecting method is not suitable for a case where a strict analysis result is demanded, but this method easily enables setting the region of an endothelial cell as compared with the apex input method. Further, it is advantageous in a case where an examiner wants to recognize a rough density from a single cell.

Herein, the grid method and the trace method mentioned as the other examples of the cell region setting mode are briefly introduced. The grid method including superimposing a square grid of a predetermined size on a photographed endothelium image, counting the number of cells included in the grid, and inversely calculating an average cell area from the average number of cell area. The grid method enables relatively easily obtaining the cell density and the average cell area in units of grid, but the degree distribution such as a cell area cannot be measured. The trace method includes making an examiner trace the profile of a cell visually recognized in the photographed image on the touch panel and others so that the apparatus obtains the profile information, thereby setting the cell profile based on the profile information. This trace method is suitable for the same purpose as for the apex input method.

According to the above setting modes, it is possible to set the boundary of each cell as a result according to the above-described input command, thus enabling analysis of the size and the shape of each cell, and others, and the characteristic of each cell. In the present embodiment, the control part 1 may perform the setting processing of cell profile based on the input command and the analysis processing with respect to the set cell region at the same timing or at different timing according to an operation command.

Upon completion of the analysis processing, the control part 1 further changes over the display of the monitor 5 to the basic screen 200, and outputs (i.e., displays) the analysis processing results on the analysis result display section 210 and the distribution graph display section 220. When a cancel button 269 arranged adjacent to the OK button 268 is touched, the manual analysis is terminated without performing analysis and the display of the monitor 5 is changed over to the basic screen 200.

When the endothelial cell region is set by the two or more types of setting modes (that is, at least a first setting mode and a second setting mode) per one endothelial cell image, the control part 1 in the present embodiment at least temporarily stores, in the storage part 2, the information on the cell region set by the first setting mode with respect to one endothelial cell image and the information on the cell region set by the second setting mode. The information stored in the storage part 2 may be for example the positional information of each cell region (concretely, the profile of each cell) or the analysis result information per setting mode.

Further, when the endothelial cell region is set by the two or more types of setting modes (that is, at least the first setting mode and the second setting mode) with respect to one endothelial cell image, the control part 1 can integrate the regions of endothelial cells set individually by the setting modes. In this case, the control part 1 in the present embodiment obtains an analysis result on the endothelial cells of an examinee's eye with respect to an integrated result. For instance, on an image of one endothelial cell image, the first setting mode is used for the cell image formed in the first image region and the second setting mode is used for the cell image formed in the second image region different from the first image region. It is to be noted that the second image region is formed in a different region from the first image region. In this case, the integrated result includes both the endothelial cell region set in the first image region and the endothelial cell region set in the second image region.

In the present embodiment, when the analysis processing is to be performed, the analysis processing is conducted while the setting result by the first setting mode and the setting result by the second setting mode are integrated. As the setting result, in more detail, the positional information of the profile of each cell is conceivable. The analysis processing may be any processing capable of producing an analysis result with respect to an integrated result of the endothelial cell regions. The analysis does not need to be performed for the integrated region of the setting result by the first setting mode and the setting result by the second setting mode. For instance, the analysis processing may be performed by separately determining the first analysis result based on the first setting mode and the second analysis result based on the second setting mode, and then integrating those analysis results.

In the present embodiment, when the setting target for which the cell region is set by the first setting mode and the setting target for which the cell region is set by the second setting mode are commanded in order by an examiner, the control part 1 sets the cell region with respect to each of the setting targets by using the corresponding setting mode suitable for each setting target.

For example, after the control part 1 receives a selection command of the setting target for which the cell region is set by the first setting mode (e.g., the operation of inputting the positions of the center point of an endothelial cell, the apex of the profile, and others, the operation of placing the reference pattern P on the endothelial cell image 261, and others), when the cell-region setting mode is changed over to the second setting mode at the touch of the button 263a, 263b, or 263c, the control 1 holds the information representing the cell-region setting target by the first setting mode. In this case, the control part 1 in the present embodiment may continue to display the image information (e.g., the mark D indicating the center point, the cell image Ca, Cp, and others) representing the setting target by the first setting mode while the control part 1 receives a command of the setting target for which the cell region is set by the second setting mode. After receiving a command to select the setting target for which the cell region is set by the second setting mode, upon touch of the OK button 268, the control part 1 sets a cell region to each of the setting targets. As a result, the endothelial cell regions set by the first setting mode and the endothelial cell regions set by the second setting mode are integrated. Thereafter, the control part 1 performs analysis based on the integrated endothelial cell regions and stores an analysis result thereof in the storage part 2.

Figure 4:
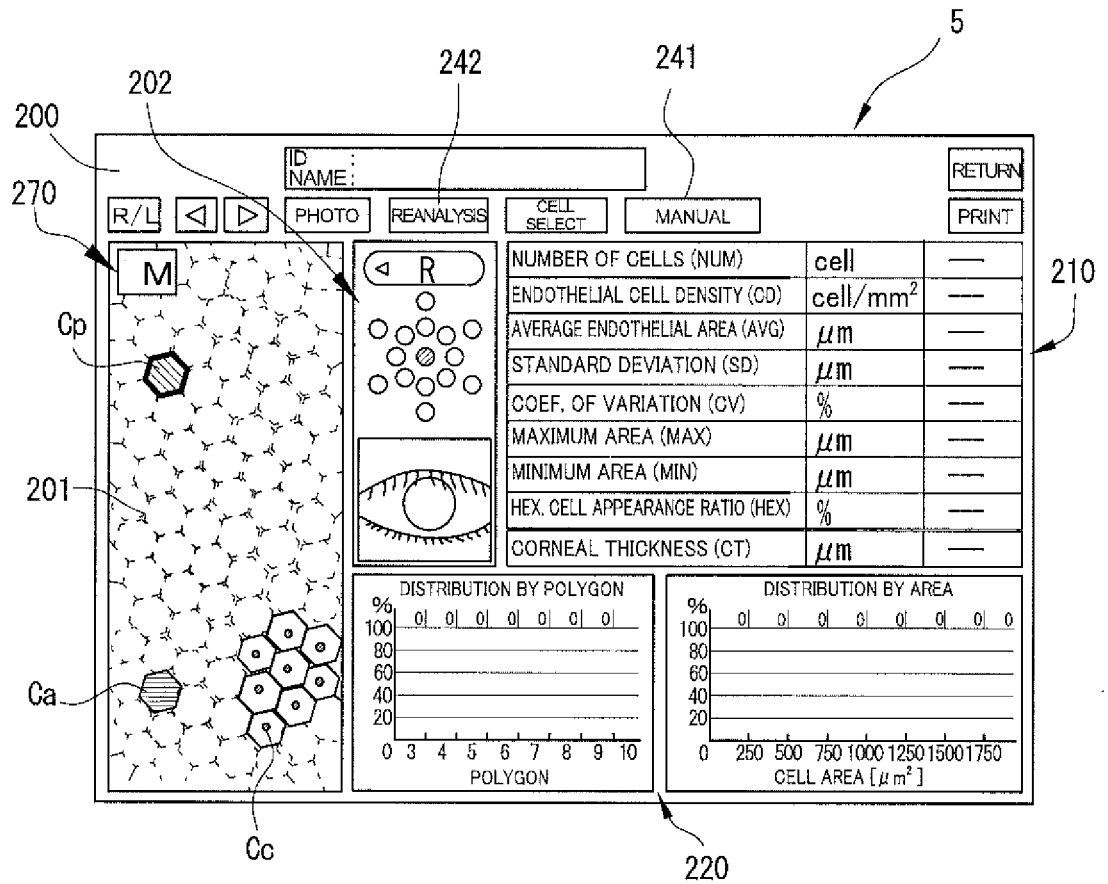
FIG. 4 is a schematic diagram showing a basic screen displaying results of manual analysis obtained by integration of a plurality of analysis methods.
Figure 5:
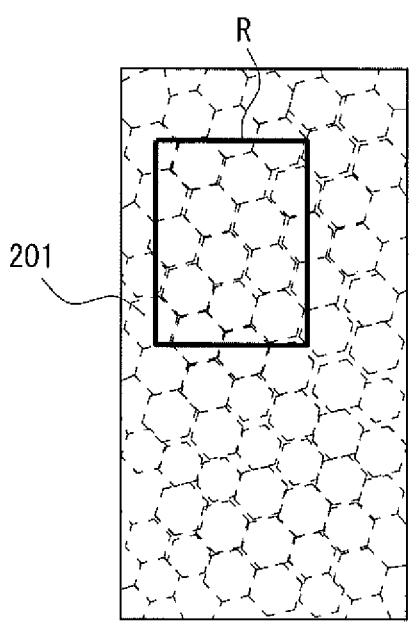
FIG. 5 is a schematic diagram showing a part of an endothelial cell image in which an automatic analysis range is set.
Figure 6:
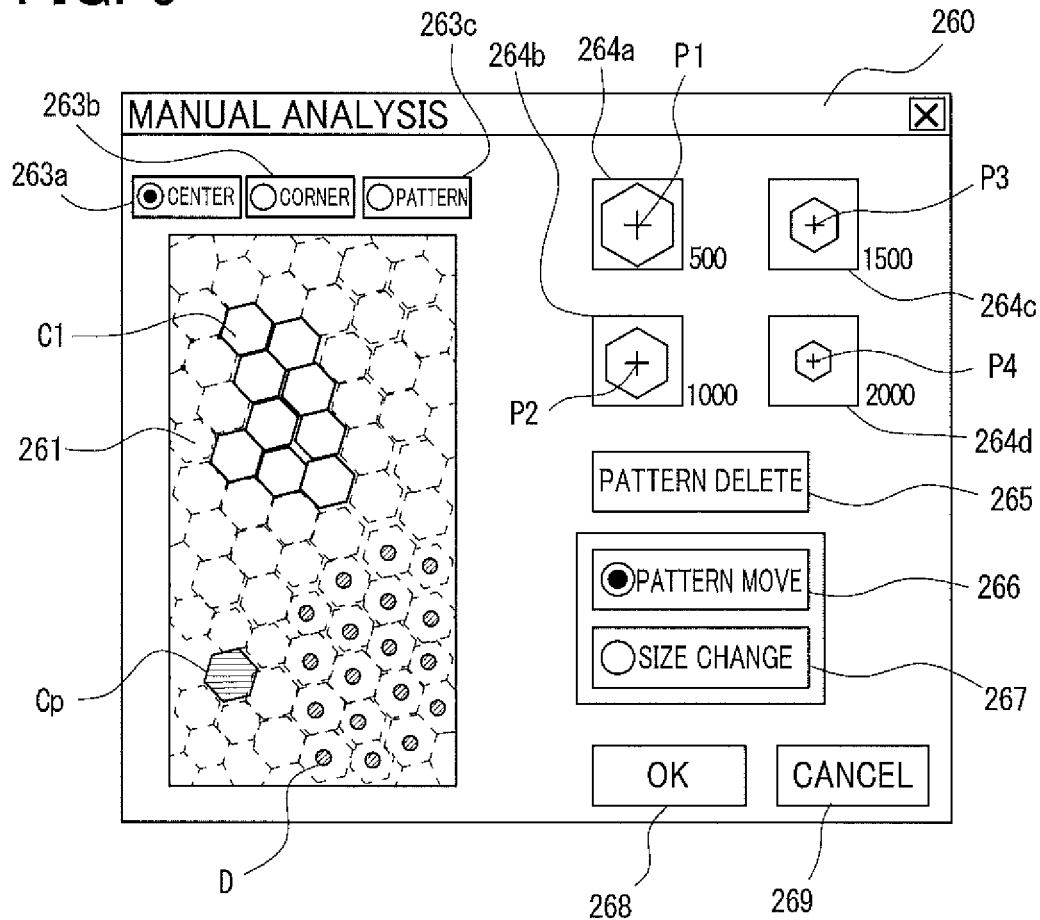
FIG. 6 is a schematic diagram showing a manual analysis screen appearing when integrative analysis of automatic analysis and manual analysis is performed.

After execution of the analysis, the control part 1 displays the basic screen 200 on the monitor 5 and displays the analysis result of the integrated endothelial cell regions on the analysis result display section 210 and the distribution graph display section 220. When the endothelial cell regions are to be set by two or more types of setting modes with respect to one endothelial cell image, the control part 1 further integrally displays the cell images C (that is, at least two types of cell images Cc, Ca, and Cp) each indicating the endothelial cell regions set by the corresponding setting mode on one photographed image (herein, on the endothelial cell image 201 of the basic screen 200). Accordingly, the examiner can easily perceive the endothelial cells used in the analysis. As shown in FIG. 4, the cell images Cc, Ca, and Cp may be indicated in different display patterns according to the used setting modes.

In the above manner, the manual settings of two or more types can be performed with respect to one endothelial cell image. This can improve both the reliability of analysis results and the efficiency of input work. For instance, in one endothelial image, the setting by the center method can be performed in the first image region in which the cells are packed closely at an extent to which the center method is executable, and the setting by the apex input method or pattern input method can be performed in the second image region which is apart from the first image region and in which the cells are not packed closely in a constant area. Furthermore, in the second image region, according to the cell shape and others, the apex input method or pattern input method may be selectively used. Since the setting results by the setting modes are integrated, the analysis result related to one whole endothelial cell image can be obtained.

<Integration of Automatic Analysis and Manual Analysis>

A case of integrally performing automatic analysis and manual analysis will be explained below. The control part 1 in the present embodiment integrates the regions of endothelial cells detected by the control part 1 during automatic analysis and the regions of endothelial cells set by any one of the setting modes by the control part 1 during manual analysis with respect to one endothelial cell image. In this case, the integrated result includes both the regions of endothelial cells detected by the automatic analysis and the regions of endothelial cells set during the manual analysis. The control part 1 further obtains an analysis result related to the endothelial cells of an examinee's eye based on the integrated endothelial cell regions. According to the analysis apparatus 100 in the present embodiment, it is possible to analyze the regions of endothelial cells not targeted for detection manually added to the regions of endothelial cells detected by the previous automatic analysis.

Herein, the analysis apparatus 100 in the present embodiment can change an execution range of the automatic analysis (from the whole range of the endothelial cell image 201). For instance, the control part 1 receives, via the input part 4, a command of an execution area R of the automatic analysis (referred to as an automatic analysis range R) with respect to the endothelial cell image 201. In the present embodiment, when the control part 1 receives a drag operation with respect to the endothelial cell image 201 on the monitor 5, the control part 1 sets a rectangular automatic analysis area R. However, the operation to designate the automatic analysis area R and the shape of the automatic analysis area R to be set according to that operation are not limited to the above examples. In the present embodiment, when the automatic analysis area R is set, a graphic (e.g., a frame line) representing the automatic analysis area R is displayed by superimposing on the endothelial cell image 201 on the monitor 5. It is to be noted that the automatic analysis area R may be set at one or more places in one endothelial cell image 201. In the present embodiment, the result of the automatic analysis related to the endothelial image included in the automatic analysis area R and the detection result of endothelial cells are displayed on the basic screen 200 when a re-analysis button 242 is touched.

In the present embodiment, the examiner determines whether or not the automatic analysis area R is set in a part of the endothelial cell image 201 from various information such as the endothelial cell image 201 and others displayed on the basic screen 200. For instance, in the endothelial cell image 201, the automatic analysis area R is set at a place in which the regions of endothelial cells are detected well by the automatic analysis and the regions of endothelial cells are set manually at a place in which the regions of endothelial cells are not properly detected. This can provide both the efficiency of analysis work and the analysis accuracy.

When the regions of endothelial cells are detected by the automatic analysis in the whole endothelial cell image 201 or the automatic analysis range R, in the endothelial cell image 261 on the manual analysis screen 260, the cell images C1 are superimposed on the detected regions of endothelial cells by the automatic analysis. In this state, the regions of endothelial cells to be analyzed in the endothelial cell image 261 are manually added. In the present embodiment, the control part 1 sets a new region(s) of endothelial cell(s) by using at least one of the above-described three types of setting modes. Specifically, in the present embodiment, the control part 1 can set the new regions of endothelial cells by combining two or more types of setting modes selected by an examiner.

In the present embodiment, the control part 1 sets the regions of endothelial cells according to a command from the examiner so as to avoid the regions of endothelial cells detected by the automatic analysis. To be concrete, the endothelial cell regions are manually set in a range where the regions do not overlap at all the endothelial cell regions detected by the automatic analysis or in a range where an overlapping amount (e.g., the area) is an allowable range or less. Thus, it is prohibited to manually set the endothelial cell region at the displayed position of the cell image C1 automatically detected. When the automatic analysis range R is set, the control part 1 may set the endothelial cell region(s) by manual operation so as to avoid the automatic analysis range R.

In the manual analysis screen 260, when the region of at least one endothelial cell is specified and then the OK button 268 is operated, the endothelial cell region detected during the automatic analysis and the endothelial cell region(s) set during the manual analysis are integrated by the control part 1. The control part 1 further analyzes the endothelial cells of an examinee's eye based on the integrated endothelial cell regions and stores an analysis result in the storage part 2.

Figure 7:
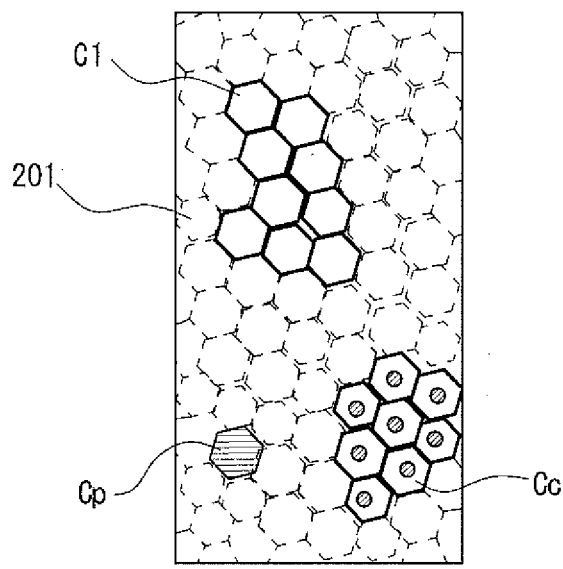
FIG. 7 is a schematic diagram showing a cornea endothelial image created by integration of an automatic analysis detection result and a set result of a cell region in the manual analysis.

On the analysis result display section 210 and the distribution graph display section 220 of the basic screen 200 displayed after execution of analysis, the integrated analysis result is displayed by the control part 1. As shown in FIG. 7, furthermore, the cell image C1 detected by the automatic analysis with respect to one endothelial cell image 201 and any one of the cell images Cc, Ca, and Cp indicating the endothelial cell regions manually set are integrally displayed in the endothelial cell image 201.

The analysis processing in this case may be any processing if only it is possible to produce an analysis result on the integrated endothelial cell regions including the endothelial cell region detected during the automatic analysis and the endothelial cell region set during the manual analysis. In the analysis processing, therefore, it is not necessary to analyze previously integrated cell regions. For instance, the analysis processing may be a processing of separately determining an analysis result by the automatic analysis and an analysis result by the manual analysis and integrating those analysis results.

<Display of Analysis Method on Analysis Result Screen>

In the present embodiment, the basic screen 200 displays manual execution information 270 indicating whether or not the analysis result displayed in the analysis result display section 210 and others include a manual analysis result (that is, whether or not the analysis result on the endothelial cell region set manually) along with the analysis result.

In the present embodiment, when only the manual analysis result is included in the analysis result displayed in the analysis result display section 210 and others, a sign "M" is indicated as the manual execution information 270 (see FIG. 4). When the analysis result displayed in the analysis result display section 210 and others corresponds to the integrated analysis result of automatic analysis and manual analysis, a sign "+M" is indicated as the manual execution information 270.

Furthermore, the manual execution information 270 may include the information representing the type of a setting mode of the manual analysis used in the analysis. For instance, when the analysis target includes the endothelial cell region(s) set by the center method, a sign "C" appears. When the analysis target includes the endothelial cell region(s) set by the apex input method, a sign "A" appears. Alternatively, when the analysis target includes the endothelial cell region(s) set by the pattern selecting method, a sign "P" appears. Since the manual execution information 270 is displayed together with the analysis result, it is easy to perceive what analysis has been made with respect to the endothelial cell image 210. The manual execution information 270 in the present embodiment is character information, but it is not limited thereto and may be graphic information.

A second embodiment of the present disclosure will be explained below. In the following explanation, similar or identical parts to those in the first embodiment are assigned the same reference signs as those in the first embodiment and their explanations are omitted. In the second embodiment, for separate image regions included in one endothelial cell image, the analysis apparatus 100 obtains individual analysis results for each of the image regions based on respective endothelial cell regions set in the image regions. The analysis apparatus 100 in the second embodiment individually displays the analysis results on the image regions on the monitor 5. Consequently, an examiner can well obtain information on local sites of the corneal endothelium. In this case, two or more types of setting modes may be used for one endothelial cell image and the endothelial cell regions may be set manually. The image regions to be individually analyzed may be perfectly separated from each other or may partly overlap.

Figure 8:
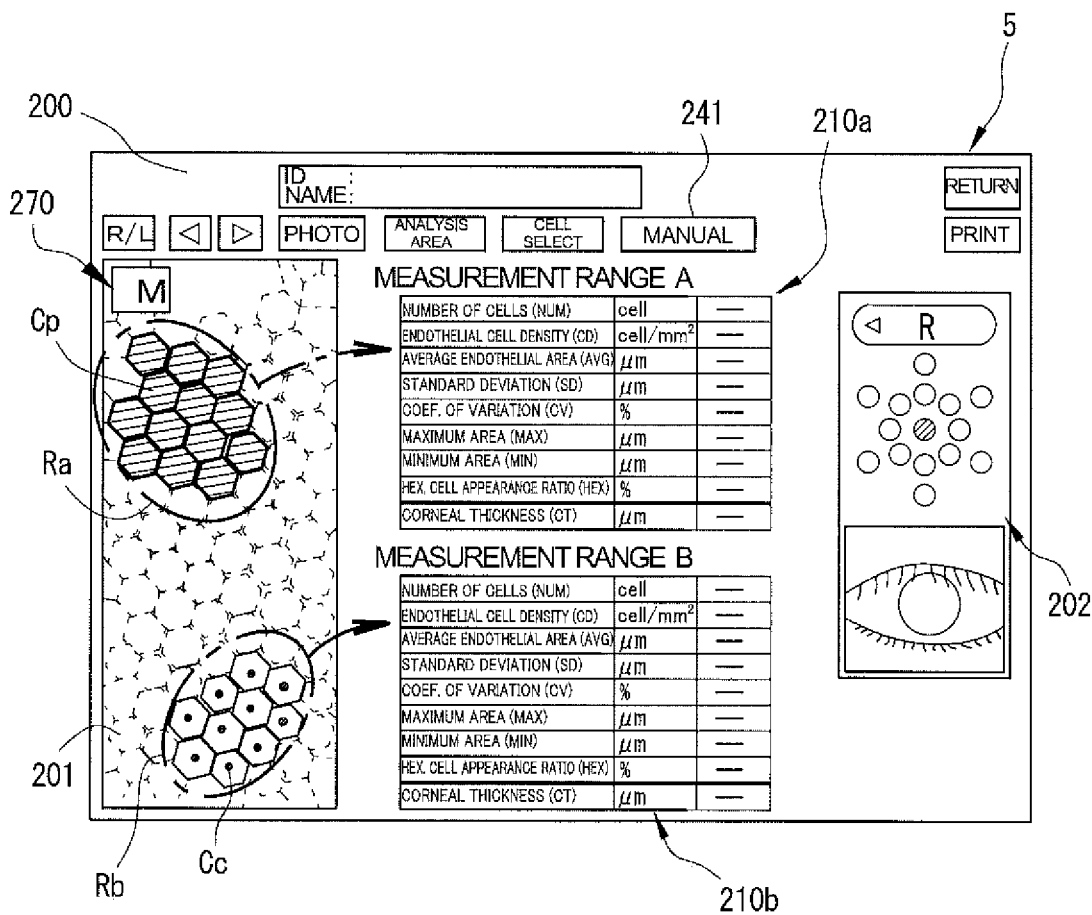
FIG. 8 is a diagram to explain a basic screen in a second embodiment.

Herein, a concrete example will be explained, referring to FIG. 8. In FIG. 8, on the basic screen 200, an image region Ra and an image region Rb included in one endothelial cell image 201 are each subjected to endothelial cell region setting (concretely, profile setting) by the control part 1. The cell region setting of each of the image regions Ra and Rb may be performed by use of the manual analysis screen 260 (see FIG. 3) as in the first embodiment. In FIG. 8, only the cell regions set by use of the apex input method are included in the image region Ra and also only the cell regions set by use of the center method are included in the image region Rb. In this case, the control part 1 causes the storage part 2 to at least temporarily store both the information on the cell regions set by the first setting mode on one endothelial cell image (e.g., positional information of each cell region, analysis result information by each setting mode, and others) and the information on the cell regions set by the second setting mode.

The basic screen 200 displays a first analysis result display section 210*a* indicating an analysis processing result with respect to the image region Ra and a second analysis result display section 210*b* indicating an analysis processing result with respect to the image region Rb. As in the first embodiment, a histogram related to the endothelial cells included in each of the image region Ra and the image region Rb (e.g., a histogram showing distributions of variation in polygonal shape, variation in cell area, and others) may be displayed as individual analysis results one for each of the image regions.

In the second embodiment, the positions of the image regions Ra and Rb are set by the control part 1 according to a command from an examiner. For instance, each of the image regions Ra and Rb may be set based on the boundary position information (e.g., coordinate information of the boundary on the endothelial cell image 201) of each image region Ra and Rb received by the control part 1 via a touch panel or the like.

The second embodiment is explained for the case of individually analyzing two image regions Ra and Rb included in one endothelial cell image. However, the analysis may be performed on three or more image regions individually.

The present disclosure is explained based on the embodiments but is not limited thereto. This disclosure may be embodied in other specific forms without departing from the essential characteristics thereof.

For instance, in the above-described second embodiment, an explanation is given to the case of manually setting the cells by one type of the setting mode for each of the image regions Ra and Rb. As an alternative, it may be arranged to set the cells by two or more types of the setting modes for at least one of the image regions Ra and Rb.

The second embodiment shows the case of setting the cell regions in one endothelial cell image by use of two or more types of setting modes and then displaying simultaneously individual analysis results included in the image regions Ra and Rb. However, these analysis results are not necessarily displayed at the same time. For instance, the analysis result on the image region Ra and the analysis result on the image region Rb may be displayed at different timings. In this case, the image regions Ra and Rb may be formed at the perfectly same position. For instance, in the case where the basis screen 200 is displayed, when a command to select the setting mode used during the manual analysis is input via a touch panel or the like to the control part 1, only an analysis result with respect to the setting mode according to the selection command and a setting result of the cell regions may be displayed on the basic screen 200.

What is claimed is:

1. A corneal endothelial cell analysis method comprising:
a displaying step of displaying a photographed image including endothelial cells of a cornea of an examinee's eye on a monitor;
a setting step of setting, based on an operation signal from a user interface, boundaries of the endothelial cells for each or more than one of the cells with respect to the photographed image displayed on the monitor, the setting step including setting the boundaries of a first portion of the endothelial cells on the one photographed image by use of a first manual setting mode and setting the boundaries of a second portion of the endothelial cells on the one photographed image by a second manual setting mode, the first manual setting mode and the second manual setting mode being different manual setting modes of receiving an operation to specify at least one of a position and a shape of the region of each endothelial cell on the photographed image from the input interface, and setting the boundaries of the endothelial cells on the photographed image based on an operation signal output from the input interface, and the second manual setting mode being different from the first manual setting mode in at least one of the operation of designating at least one of the position and the shape of the boundary of each endothelial cell and the method of creating the boundaries of the endothelial cells based on the operation; and
an analysis result obtaining step of obtaining an analysis result on the endothelial cells of the examinee's eye based on the boundaries of the endothelial cells set by the first manual setting mode in the setting step and the boundaries of the endothelial cells set by the second manual setting mode in the setting step.

2. The corneal endothelial cell analysis method according to claim 1, wherein the analysis result obtaining step includes obtaining the analysis result based on the boundaries of the endothelial cells integrally including the boundaries of the endothelial cells set by the first manual setting mode and the boundaries of the endothelial cells set by the second manual setting mode.

3. The corneal endothelial cell analysis method according to claim 1, wherein the analysis result obtaining step includes obtaining an analysis result on the boundaries of the endothelial cells set by the first manual setting mode and an analysis result on the boundaries of the endothelial cells set by the second manual setting mode.

4. The corneal endothelial cell analysis method according to claim 1, wherein when the boundaries of the endothelial cells with respect to the one photographed image are to be set by the first manual setting mode and the second manual setting mode in the setting step, the method further includes a storage control step of at least temporarily storing in a memory both of information on the boundaries of the endothelial cells set by the first manual setting mode and information on the boundaries of the endothelial cells set by the second manual setting mode.

5. The corneal endothelial cell analysis method according to claim 1, further including an integrally displaying step of integrally displaying, on the one photographed image, the boundaries of the endothelial cells set by the first manual setting mode in the setting step and the boundaries of the endothelial cells set by the second manual setting mode in the setting step.

6. The corneal endothelial cell analysis method according to claim 1, further including a detection-processing step of detecting the boundary of each of the endothelial cells included in the photographed image by image processing of the photographed image,
wherein the analysis result obtaining step includes integrating the boundaries of the endothelial cells detected by the detection-processing step and the boundaries of the endothelial cells set by one of the manual setting modes in the setting step, and obtaining an analysis result on the endothelial cells of the examinee's eye based on the integrated boundaries of the endothelial cells.

7. The corneal endothelial cell analysis method according to claim 1, further including an analysis result displaying step of displaying information that the boundary of a cell to be set in the setting step has been analyzed on the monitor together with the analysis result obtained in the analysis result obtaining step.

8. The corneal endothelial cell analysis method according to claim 1, further including an analysis result displaying step of displaying information representing a setting mode for the boundary of the endothelial cell analyzed by the analysis result obtaining step on the monitor together with the analysis result obtained by the analysis result obtaining step.

9. A corneal endothelial cell analysis apparatus including a controller configured to execute the corneal endothelial cell analysis method according to claim 1.

10. The corneal endothelial cell analysis method according to claim 1, the first manual setting mode being a center method.

11. The corneal endothelial cell analysis method according to claim 1, the second manual setting mode is one of an apex input method, a pattern selecting method, a grid method, and a trace method.

* * * * *